(12) United States Patent
Sievers et al.

(10) Patent No.: US 7,473,245 B2
(45) Date of Patent: Jan. 6, 2009

(54) AORTIC CANNULA

(75) Inventors: Hans-Hinrich Sievers, Kronshagen (DE); Marcus Göllner, München (DE); Michael Wetzig, München (DE)

(73) Assignee: Sorin Group Deutschland GmbH, Munich (DE)

(*) Notice: Subject to any disclaimer, the term of this patent is extended or adjusted under 35 U.S.C. 154(b) by 3 days.

(21) Appl. No.: 10/542,472

(22) PCT Filed: Jan. 20, 2004

(86) PCT No.: PCT/EP2004/000425

§ 371 (c)(1),
(2), (4) Date: Feb. 6, 2006

(87) PCT Pub. No.: WO2004/067073

PCT Pub. Date: Aug. 12, 2004

(65) Prior Publication Data

US 2006/0142702 A1 Jun. 29, 2006

(30) Foreign Application Priority Data

Jan. 30, 2003 (DE) ............................ 103 03 744

(51) Int. Cl.
*A61M 31/00* (2006.01)
(52) U.S. Cl. .................................... 604/275; 604/4.01
(58) Field of Classification Search .................. 604/30, 604/275, 264; 600/114; 239/500, 504, 505
See application file for complete search history.

(56) References Cited

U.S. PATENT DOCUMENTS 1,877,046 A * 9/1932 Phillips ...................... 239/500

(Continued)

FOREIGN PATENT DOCUMENTS

CA 2 311 977 A1 12/2000

(Continued)

OTHER PUBLICATIONS

International Preliminary Report On Patentability.

*Primary Examiner*—Nicholas D Lucchesi
*Assistant Examiner*—Laura A Bouchelle
(74) *Attorney, Agent, or Firm*—Wolf Greenfield & Sacks, P.C.

(57) ABSTRACT

The invention relates to an aortic cannula for delivering fluid, especially blood, into a vessel of the human body, particularly the aortic arch. Said aortic cannula comprises an elongate basic cannula body into which the fluid is directed, an orifice from which the fluid is discharged at the distal end of the basic cannula body in a basic direction of flow defined by the basic cannula body, as well as at least one first deflecting element and a second deflecting element that are disposed in front of the orifice within the flow path of the fluid. Said at least one deflecting element and said second deflecting element are respectively provided with a passage opening that is aligned relative to the orifice, and a deflecting area which redirects the portion of the fluid, which does not flow through the passage opening. The area of the passage opening of the first deflecting element is greater than area of the passage opening of the second deflecting element, and/or the angle of deflection of the deflection area of the first deflecting element is greater than the angle of deflection of the deflection area of the second deflecting element which is arranged behind the first deflecting element.

32 Claims, 6 Drawing Sheets

U.S. PATENT DOCUMENTS

| | | | | |
|---|---|---|---|---|
| 2,314,754 A * | 3/1943 | Baird | ......................... | 239/500 |
| 3,225,763 A * | 12/1965 | Waterman | ................... | 604/192 |
| 5,354,288 A * | 10/1994 | Cosgrove et al. | ............ | 604/264 |
| 5,616,137 A | 4/1997 | Lindsay et al. | | |
| 5,662,619 A | 9/1997 | Zarate | | |
| 6,387,087 B1 | 5/2002 | Grooters | | |
| 2004/0035953 A1 * | 2/2004 | Nelson et al. | ............... | 239/501 |
| 2004/0267212 A1 * | 12/2004 | Jonkman | ................. | 604/275 |

FOREIGN PATENT DOCUMENTS

| | | |
|---|---|---|
| DE | 196 05 864 A1 | 8/1996 |
| DE | 199 33 171 A1 | 12/2000 |
| DE | 103 03 744 A1 | 8/2004 |
| EP | 0 705 617 A | 4/1996 |
| EP | 0 612 536 B1 | 12/1999 |
| WO | WO 99/56808 A1 | 11/1999 |
| WO | WO 2004/067073 A1 | 8/2004 |

\* cited by examiner

AORTIC CANNULA

The invention relates to an aortic cannula, in particular for use during a heart operation, for delivering fluid into the aorta.

Prior art has on numerous occasions described the problems that can occur during the delivery of fluid, in particular blood, into the aortic arch or another vessel of the human body. Reference is hereby made to DE 196 05 864 A1, WO 99/56808 A1, DE 199 33 171 A1, EP 0 612 536 A1 and EP 0 705 617 A1. These problems are primarily caused by the fluid emerging from the cannula when the fluid flows out of the distal end of a tube-like cannula in a directed manner at a very high speed. Therefore, the prior art pursued the objective of reducing the discharge velocity of the fluid and of imposing a whirling motion in the fluid flow.

For example, EP 0 612 536 describes an aortic cannula, with low flow rates in which the discharge velocity is reduced by means of a diffuser in the vicinity of the distal end of the cannula. On the one hand, it describes a diffuser in the form of a rounded cone which completely blocks the lumen at the distal end of the cannula, so that the blood delivered through the cannula is only discharged through the outlet openings arranged in the sidewall in the vicinity of the diffuser. In addition, it also describes diffusers comprising several helical splines and outlet openings matched to the helical splines. Some of these diffusers only partially block the distal opening of the lumen.

DE 196 05 864 A1 also describes an aortic cannula for low flow rates. In this case, the low flow rates are achieved by the fact that the sidewall of the cannula contains several spiral-shaped slots at the distal end, which widen or constrict in reaction to pressure changes in the cannula's lumen. The widened slots result in a reduced flow rate. In addition, there is a central opening at the distal end of the cannula which is smaller than the lumen diameter and which is wedge-shaped in the direction of the lumen and cone-shaped in the direction of flow.

EP 0 705 717 A1 describes an aortic cannula in which outlet openings are provided in the sidewall of the blood-carrying cannula while the distal end of the cannula is blocked by a cap. In the direction of the lumen, the cap is shaped so that the blood is diverted to the outlet openings.

DE 199 33 171 AI describes a cannula for delivering a fluid into the aortic arch of the human body in which the stagnation pressure of the emergent free jet is reduced by the provision of means in the cannulas which impose a linear motion and a whirling motion on the fluid particles. A twisting element is described as a suitable means behind which an equalising section or an angled section is provided in the direction of flow. The blood then emerges from the distal end of the cannula through an outlet opening on the face at the end of the cannula.

WO 99/56808 AI describes an aortic cannula with a reduced discharge velocity which is achieved in that three sidewall sections which spring back into the interior of the lumen are provided at a point at the distal end of the cannula. These sections have an opening in the direction of the proximal end so that blood flowing towards the distal end of the lumen is partially diverted through the openings and emerges from the outlet openings formed in the sidewall.

Against this background, the invention describes an aortic cannula for delivering fluid, in particular blood, into a vessel of the human body, in particular the aortic arch, with an elongate cannula body into which the fluid is directed, with an orifice, from which the fluid is discharged at the distal end of the basic cannula body in a basic direction of flow defined by the cannula body and with at least one first deflecting element and a second deflecting element, which are arranged in front of the orifice within the flow path of the fluid and which are respectively provided with a passage opening that is aligned relative to the orifice and a deflecting area which redirects the portion of the fluid which does not flow through the passage opening; wherein the area of the passage opening of the first deflecting element is greater than the area of the passage opening of the second deflecting element, and/or the angle of deflection of the deflecting area of the first deflecting element is greater than the angle of deflection of the deflecting area of the second deflecting element which is arranged behind the first deflecting element in the basic direction of flow.

The fact that, according to the invention, the size of the passage opening is reduced and/or the angle of deflection is increased from one deflecting element to the next means that in each case a portion of the fluid flowing out of the orifice is redirected from the basic flow and led off to the side which reduces the rate of flow and causes a whirling motion to take place. According to the invention, some of the outflowing fluid still passes through the passage openings directed towards the orifice along the basic direction of flow, but the stepwise separation of partial quantities of the flowing fluid at the deflecting elements also achieves a rate reduction in the portion still flowing in the basic direction of flow.

In one preferred embodiment of the aortic cannula according to the invention, the passage opening area of all the deflecting elements is smaller than or equal to the orifice's opening surface. This means the deflecting elements are at least in sections always arranged in the fluid flow discharged from the orifice.

In another preferred embodiment of the aortic cannula according to the invention, the overall diameter of the first deflecting element is greater than the overall diameter of the second deflecting element, which is arranged in the basic direction of flow behind the first deflecting element. In other words, as the distance from the orifice increases, the overall diameter of the deflecting elements decreases.

In one preferred embodiment, the area contents of the deflection surfaces on the different deflecting elements are substantially the same. This ensures that a similar amount of the fluid is deflected by the individual deflecting elements.

In conformity with a generally tube-like, cannula body, the first and second deflecting elements are advantageously in a circular shape.

In order to avoid damage from the blood delivered through the aortic cannula according to the invention, in one advantageous embodiment of the aortic cannula according to the invention, the surfaces of the first and second deflecting elements facing the orifice have a rounded shape.

A balanced ratio between the complexity of production and the desired effect is achieved according to one advantageous embodiment of the aortic cannula by the provision of four deflecting elements. Although fewer than four deflecting elements produce the desired influence on the fluid discharged through the orifice, a better result is achieved with four deflecting elements. If the number of deflecting elements is further increased, the complexity of the production technology also increases.

The introduction of the aortic cannula according to the invention into a vessel is made easier and the risk of damage to the vessel wall is reduced if, in accordance with one preferred embodiment, the deflecting element arranged at the greatest distance from the orifice on the side facing away from the orifice has a rounded surface which is penetrated by the passage opening thus achieving a rounded cannula tip.

In order to position the individual deflecting elements reliably and aligned in front of the orifice in the fluid flow, fixing elements are provided to hold deflecting elements, which extend from the orifice of the cannula substantially in the basic direction of flow and to which the deflecting elements are fixed. The fixing elements are advantageously slender to keep any unwanted influence on the fluid flow as low as possible.

On the side facing the interior of the cannula, the fixing elements have a rounded or preferably tetrahedral shape.

Preferably, the fixing elements form an outside contour to keep the inner wall of the aorta at a distance from the outer edges of the deflecting elements.

In one preferred embodiment, the deflecting elements and the fixing elements have a one-piece design, which is advantageous from the point of view of production.

According to another embodiment of the aortic cannula according to the invention, the deflecting elements and the fixing elements can be embodied as a cannula head. This cannula head can be separated from the cannula body and has a fixing section for the cannula body. The generally tube-like cannula body can be pushed onto this fastening section. A hollow-cylindrical part of the cannula head can then be considered to be a continuation of the tube-like basic cannula body encompassing the orifice in front of which the deflecting elements according to the invention are positioned.

Other designs are described in the following with reference to an example of an embodiment of an aortic cannula according to the invention. The description refers to the drawings in which.

Figure 1:
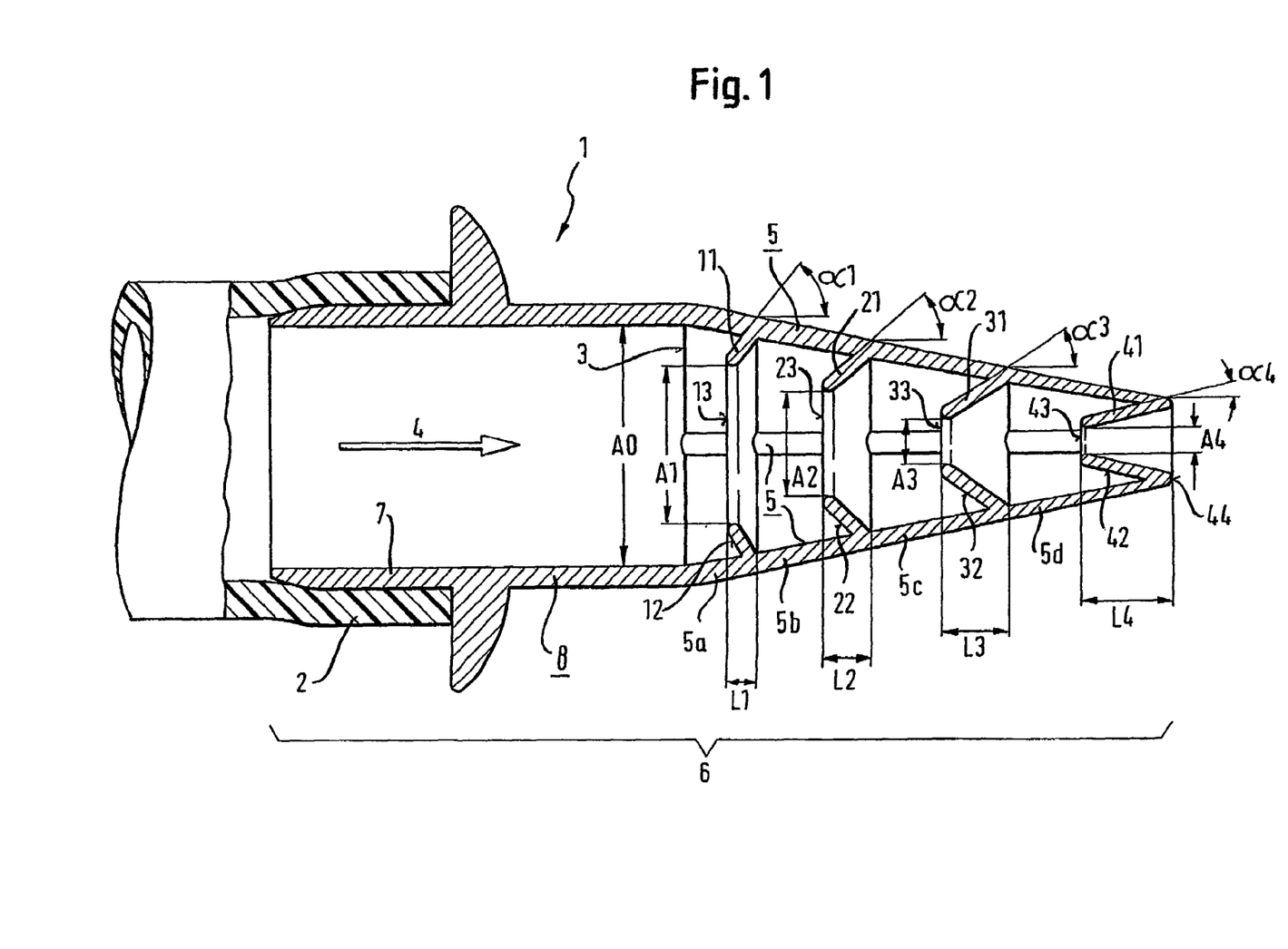
FIG. 1 is a sectional view of an aortic cannula according to the invention with four deflecting elements, which are integrated with fixing elements to a cannula tip

FIG. 1 shows an aortic cannula according to the invention 1 for delivering fluid, in particular blood, into a vessel of the human body, in particular the aortic arch. The aortic cannula according to the invention 1 comprises an elongate cannula body 2 and 8 into which the blood is directed. The cannula body 2 and 8 comprises an orifice 3 from which the blood is discharged at the distal end of the aortic cannula 1 in a basic direction of flow 4 defined by the cannula body. In addition, the aortic cannula according to the invention 1 according to the example of an embodiment in FIG. 1 comprises a first deflecting element 11 and a second deflecting element 21. The two deflecting elements 11 and 21 are arranged in front of the orifice 3 within the flow path of the fluid and each has a passage opening 13 or 23 which is aligned relative to the orifice 3. According to the invention, the second deflecting element 21 is arranged in the basic direction of flow 4 behind the first deflecting element 11. In addition, the two deflecting elements 11 and 21 both have a deflecting area 12 or 22 which redirects the portion of the fluid which does not flow through the passage opening 13 or 23. In the example of an embodiment according to the invention in FIG. 1, the area of the passage opening A1 of the first deflecting element 11 is greater than the area of the passage opening A2 of the second deflecting element 21. In addition, in the example of an embodiment of the invention in FIG. 1, the angle of deflection $\alpha_1$ of the deflecting area 12 of the first deflecting element 11 is greater than the angle of deflection $\alpha_2$ of the deflecting area 22 of the second deflecting element 21. This embodiment of the aortic cannula 1 according to the invention ensures that the fluid jet is successively divided and hence the volume flow through the core area of the front part of the cannula and the velocity of the flowing fluid decrease in each stage.

In this description of an example of an embodiment of the invention, the angle of deflection means the angle adopted by the surface of a deflecting element diverting the fluid flow with the basic direction of flow. In the case of an even deflecting area, the angles of deflection in FIG. 1 are specified. In the case of uneven deflecting areas, selected tangents or the direction of flow of the established deflected fluid flow may be used to define the angle of deflection.

In addition to the first and the second deflecting element 11 and 21 already discussed, the example of an embodiment of an aortic cannula according to the invention in FIG. 1 comprises a third and a fourth deflecting element 31 and 41. These deflecting elements are also arranged in front of the orifice 3 within the flow path of the fluid; the passage openings 33 or 43 are aligned relative to the orifice 3. In a continuation of the embodiment of the first and the second deflecting element 11 and 21, with the third or fourth deflecting element 31 and 41, the respective area of the passage opening A3 or A4 is again smaller than the area of the passage opening of the deflecting element in front of it relative to the basic flow. In other words, the example of an embodiment of an aortic cannula 1 according to the invention in FIG. 1 has four series-connected deflecting elements 11, 21, 31 and 41 in which the passage opening areas A1, A2, A3 and A4 decrease from one deflecting element to the next, as do the angles of deflection $\alpha_1$, $\alpha_2$, $\alpha_3$ and $\alpha_4$. It is obvious that fewer than four or more than four deflecting elements could be used in identical or modified applications of this design principle, if this makes sense in individual cases for the implementation of an aortic cannula according to the invention.

FIG. 1 also shows that, with the example of an embodiment shown here, the area of the passage opening A1, A2, A3 and A4 for all the deflecting elements 11, 21, 31 and 41 is smaller than the opening surface AO of the orifice 3. The area of the passage opening A1 of the first deflecting element 11 can, however, also be equal in size to the opening surface AO of the orifice 3 or slightly larger.

In the example of an embodiment shown in FIG. 1, the overall size of the deflecting elements 11, 21, 31 and 41 is selected so that all the deflecting elements, including the first deflecting element 11, are smaller than the orifice 3 of the basic cannula body. In one advantageous embodiment, the overall size of the first deflecting element 11 is equal to that of the orifice 3. This produces the embodiment in FIG. 1, in which the overall size of the first deflecting element 11 substantially corresponds to the orifice 3 and the other deflecting elements 21, 31 and 41 become gradually smaller and hence follow the decreasing size of the passage openings A1, A2, A3 and A4.

In addition, in the example of an embodiment of the invention in FIG. 1, the deflecting elements are designed so that their extension L1, L2, L3, L4 in the basic direction of flow 4 also increases.

Figure 2A:
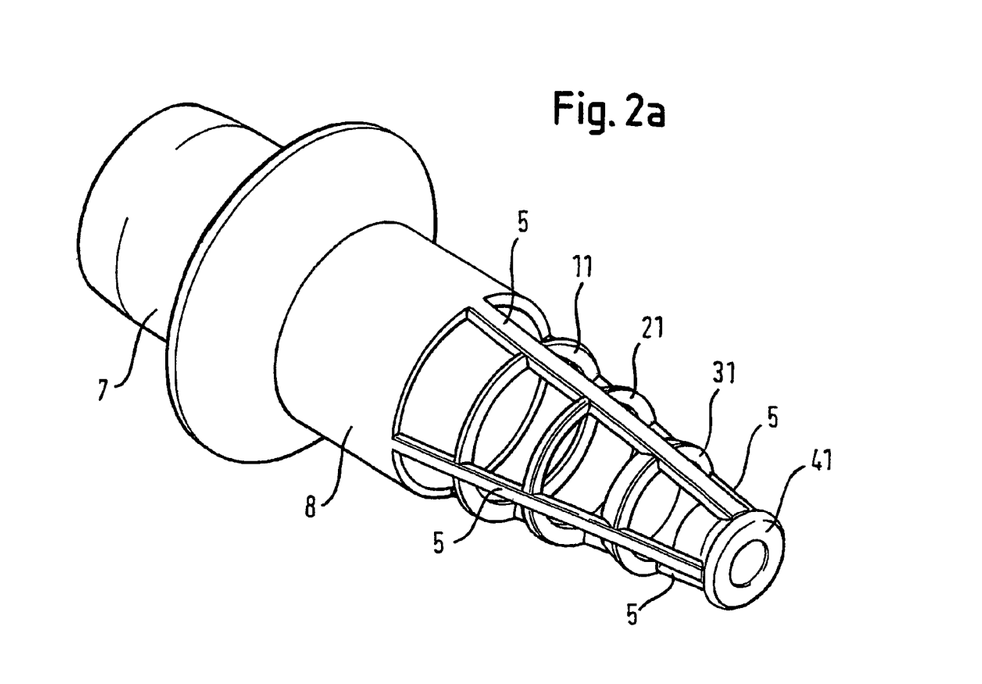
FIG. 2a is a first perspective view of the cannula tip in FIG. 1
Figure 2B:
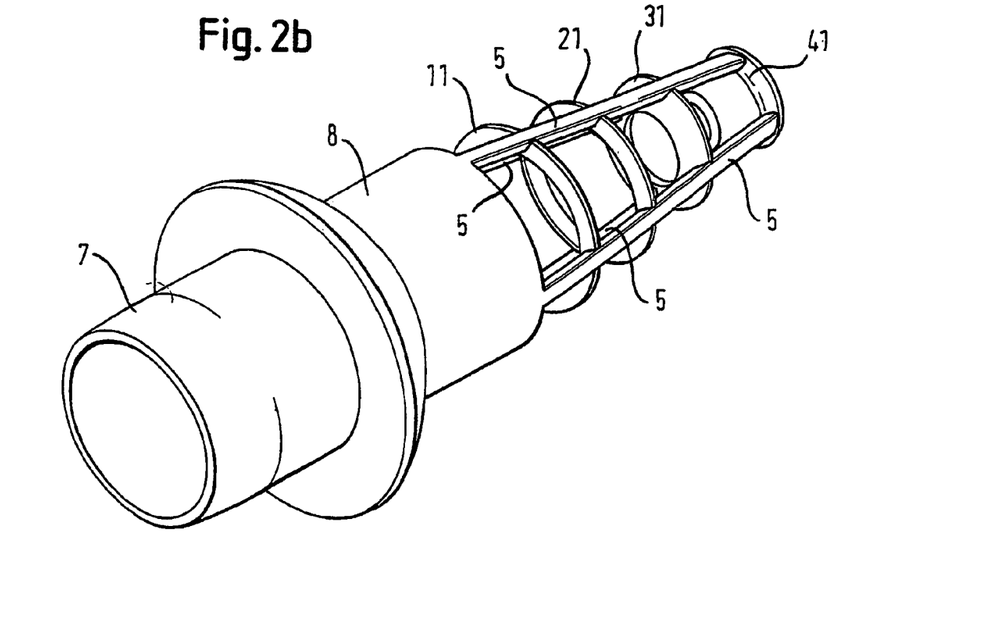
FIG. 2b is a second perspective view of cannula tip in FIG. 1

FIG. 1 also shows that in the example of an embodiment shown here the deflecting elements 11, 21, 31 and 41 have a circular shape. The circumstance is also, and in particular, evident from the perspective views 2a and 2b, which will be discussed in more detail below.

In order to protect the fluid, in particular the blood, which is delivered by the aortic cannula 1 according to the invention and is discharged at the orifice 3, the surfaces 12, 22, 32, 42 of the deflecting elements 11, 21, 31, 41 facing the orifice 3 are rounded. This surface design should, in principle, always be given preference if the basic flow of the fluid is directed straight onto a surface. Consequently, the surfaces of the fixing elements 5, which are described in more detail below, and which face the fluid flow are also preferably rounded.

In this example of an embodiment of an aortic cannula according to the invention 1, the fixing elements 5 are rods 5 to the outer edges of which the deflecting elements 11, 21, 31 and 41 are fixed, for example. The rods 5 extend from the orifice 3 of the basic cannula body 2 or 8 substantially in the basic direction of flow 4. In the example of an embodiment in FIG. 1, there are four fixing elements 5, of which only three are shown in the truncated representation in FIG. 1. The four fixing rods 5 can be identified in the perspective views in FIGS. 2a and 2b, even if the rods 5 sometimes overlap each other.

Advantageous from the point of view of production technology is a one-piece embodiment of the fixing elements 5 and the deflecting elements 11, 21, 31 and 41. In a continuation of this concept, a cannula head 6 can be formed if, in addition to this, the fixing elements 5 are embodied in one piece with a hollow-cylindrical part 8 with a fastening section 7 for a tube-like cannula body 2. When the cannula tube 2 is placed on the fastening section 7, the hollow-cylindrical part 8 of the cannula head 6 forms an extension of the cannula body 2 as far as the orifice 3; with this embodiment, the two elements should then be treated as the cannula body. The advantage of this type of embodiment consists in the fact that the cannula head 6, which encompasses the hollow-cylindrical part 8, the fixing elements 5 and the deflecting elements 11, 21, 31 and 41, is produced in one piece but independently of the other components of the aortic cannula and can then be securely connected to the cannula tube 2 in a simple way.

Figure 3:
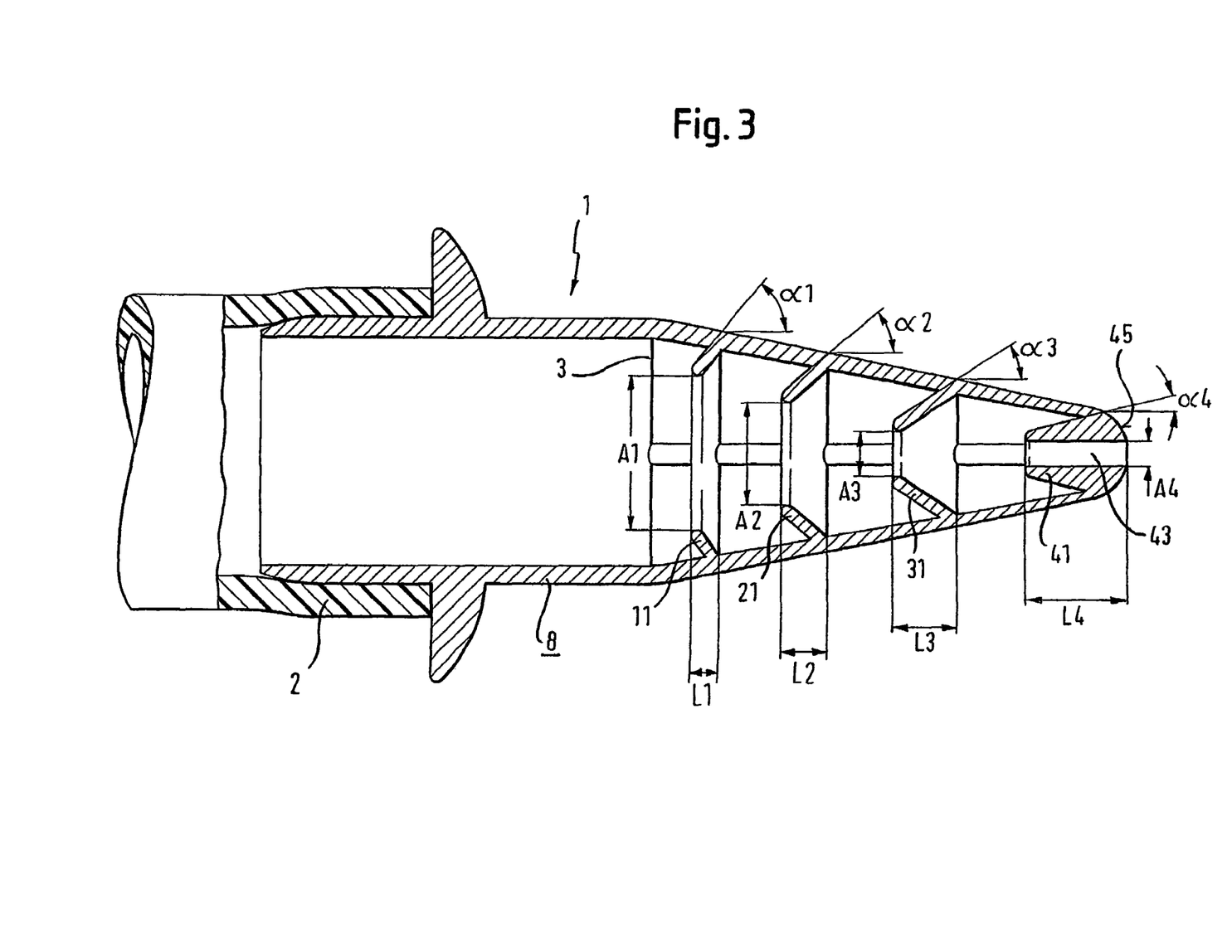
FIG. 3 is a partial view of the cannula tip in FIG. 1 in which the foremost deflecting element is provided with a rounded surface

In another embodiment of the aortic cannula according to the invention 1 according to FIG. 3, the deflecting element, which in the basic direction of flow is arranged furthest away from the orifice, in this case, therefore, the fourth deflecting element 41, is equipped with a rounded tip 45 on the side 44 facing away from the orifice 3. This ensures that on the introduction of the aortic cannula into a vessel, the risk of damage to the inner wall of the vessel is further reduced.

Although the diagrams show that, with the example of an embodiment described here, four fixing elements 5 are provided, it is automatically evident that fewer or more than four fixing elements 5 could be used. With regard to the space between the deflecting elements 11, 21, 31 and 41, it should be noted that the fixing element sections 5a, 5b, 5c, 5d in these areas may be arranged offset to each other from one area to the next, so that, unlike the examples of embodiments shown in the diagrams, there are no continuously straight fixing elements 5 running from the orifice 3 to the last deflecting element 41. FIGS. 2a and 2b also show that the fixing rods also run conically in the direction of the interior space defined by the passage openings A1, A2, A3 and A4, advantageously however, without forming a sharp edge. Instead, a preferred embodiment is a rounded embodiment of the fixing rods 5 extending inwards, which results in an essentially triangular cross-section of the rods 5.

In a specific example of an embodiment, the deflecting elements 11, 21, 31 and 41 are arranged about 1.5 to 3 mm apart in the basic direction of flow 4. In the case of a cannula with an approximately 8 mm external diameter, the internal diameter and the angle of deflection of the deflecting elements 11, 21, 31 and 41 are as shown by way of example in the following table:

| Deflecting elements (reference numbers) | Diameter of the passage opening | Angle of deflection |
| --- | --- | --- |
| 11 | 5.0-6.5 mm | 80-50 |
| 21 | 4.0-5.5 mm | 60-40 |
| 31 | 3.0-4.5 mm | 45-25 |
| 41 | 1.0-3.5 mm | 35-15 |

The diameters have to be adjusted appropriately for smaller or larger embodiments.

Figure 4:
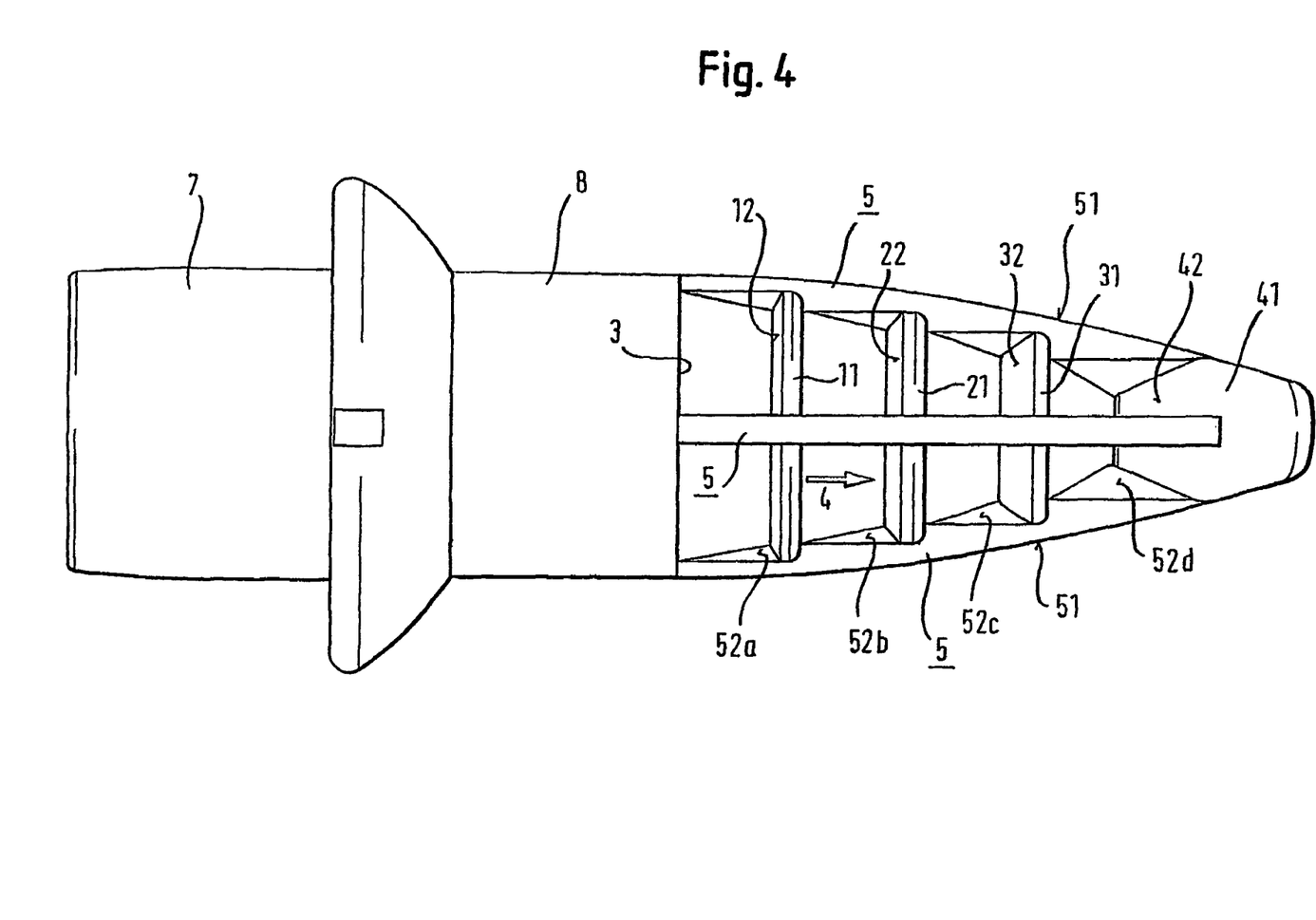
FIG. 4 is a side view of a second example of an embodiment of an aortic cannula according to the invention with four deflecting elements, which are integrated with fixing elements to a cannula tip

FIG. 4 shows a second example of an embodiment of an aortic cannula according to the invention. As with the first example of an embodiment, the aortic cannula comprises several deflecting elements 11, 21, 31, 41, which are arranged in front of the orifice 3 within the flow path of the fluid. The second example of an embodiment also has deflecting areas 12, 22, 32, 42 on the side of the deflecting elements 11, 21, 31, 41 facing the orifice. The angles of deflection $\alpha_1$, $\alpha_2$, $\alpha_3$ and $\alpha_4$ (see FIG. 1), which are adopted by the deflecting areas 12, 22, 32, 42 with the basic direction of flow 4 become smaller as the distance of the deflecting element 11, 21, 31, 41 from the orifice 3 increases.

Figure 5:
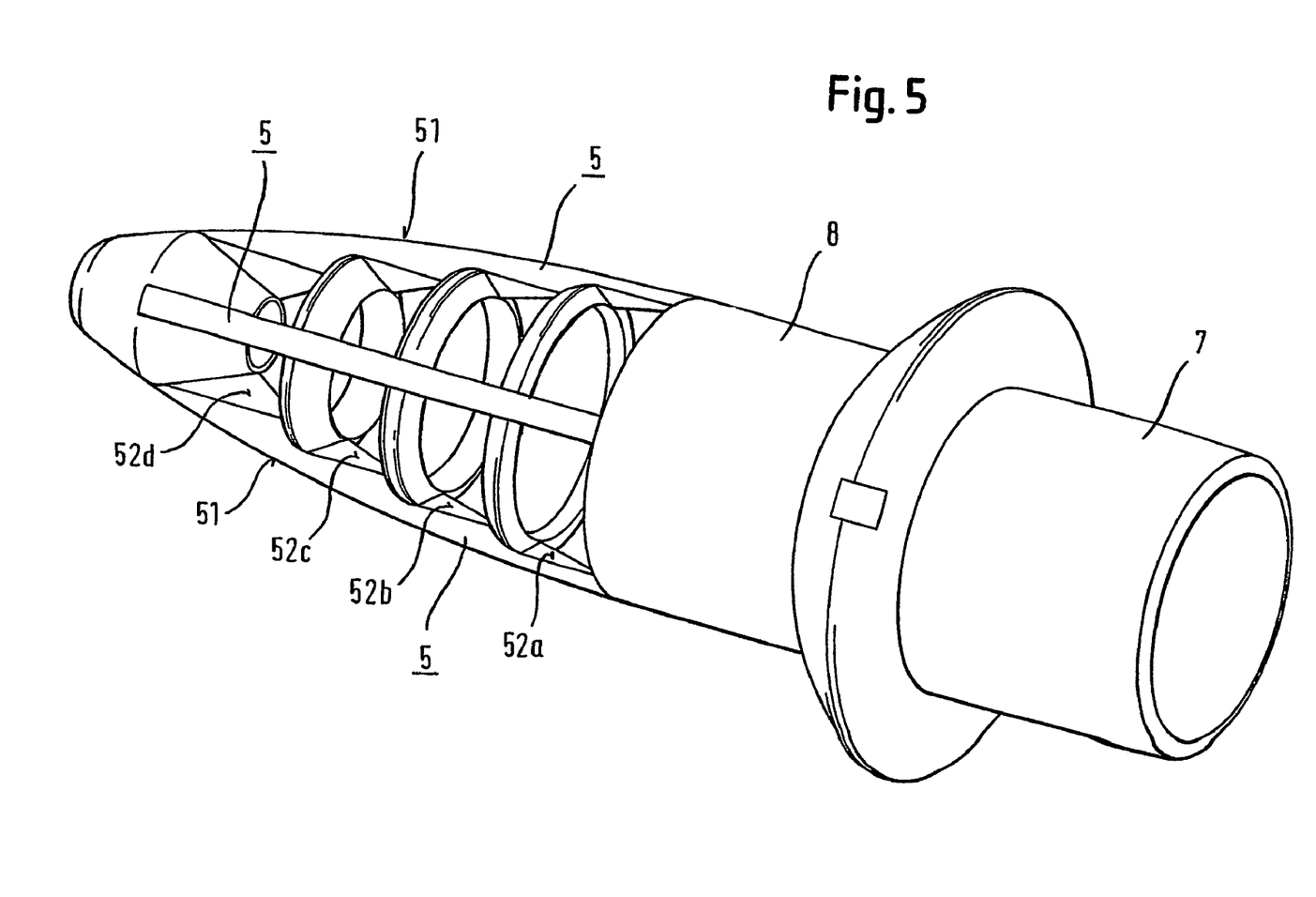
FIG. 5 is a perspective view of the second example of an embodiment of an aortic cannula according to the invention.

In the second example of an embodiment, the fixing elements 5 are designed more generously. As shown in FIG. 4, the fixing rods 5 extend over the immediate extension of the deflecting elements 11, 21, 31, 41 thus forming an outside contour 51 which is able to extend continuously into the tip of the aortic cannula. As is particularly evident in FIG. 4, this provides a body which is advantageous for the introduction of the aortic cannula. The outside contour 51 of the fixing rods 5 ensures that there is a space between the inner wall of the aorta and the outer surfaces or edges of the deflecting elements 11, 21, 31, 41. The continuous transition of the outside contour 51 into the cannula tip is also clearly evident in FIG. 5.

On the side facing the interior of the cannula, the fixing rods 5 in the example of an embodiment according to FIG. 4 have a tetrahedral surface 52a, 52b, 52c, 52d. This embodiment of the side of the fixing rods 5 facing the fluid flow is also clearly shown in FIG. 5. The tetrahedron imposed on these surfaces has been selected so that it tapers towards the orifice 3 and hence its height decreases. On the side facing away from the orifice 3, the tetrahedron is brought forward as far as the edge of the passage opening of the respective deflecting element 11, 21, 31, 41.

Figure 6:
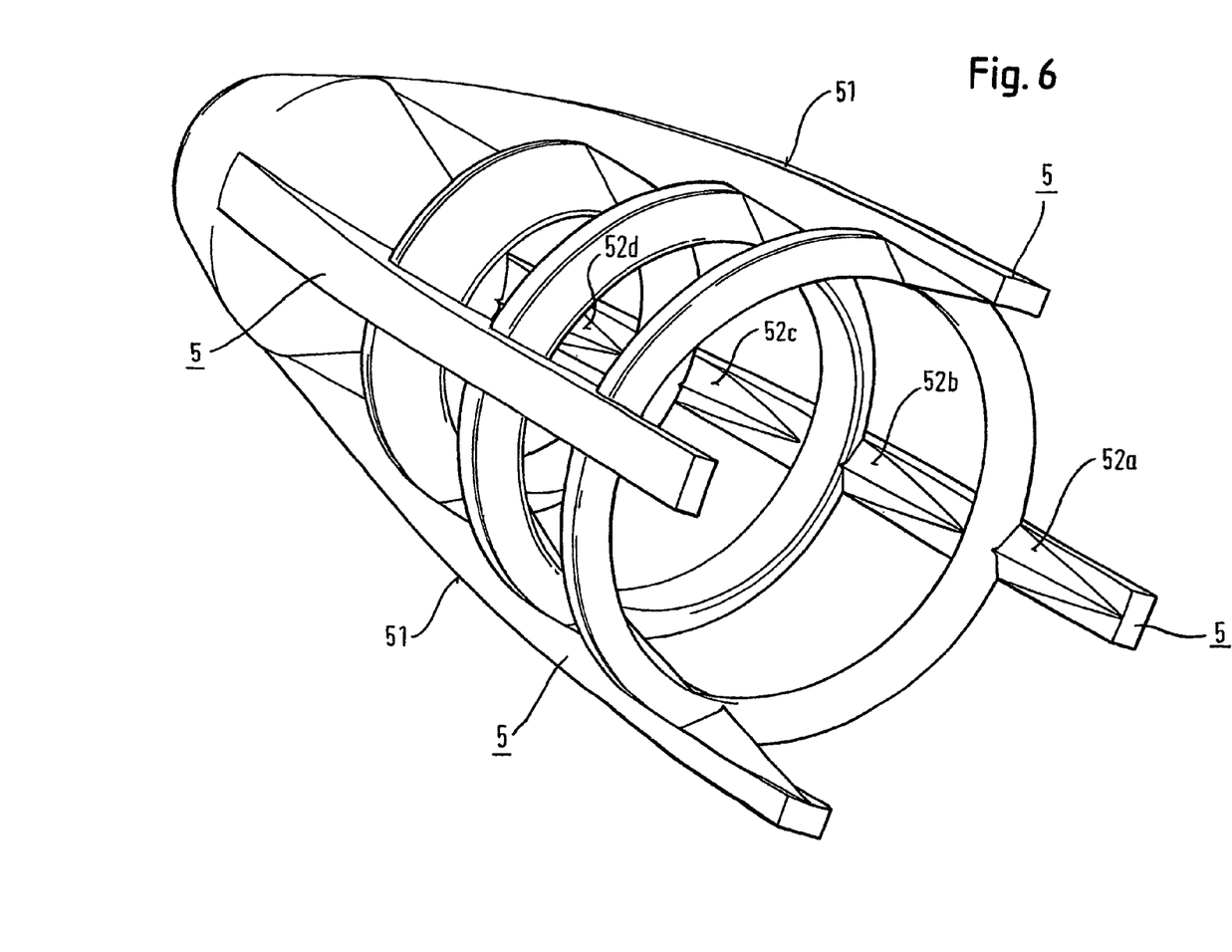
FIG. 6 is a perspective view of a part of the second example of an embodiment of an aortic cannula according to the invention.

To clarify this embodiment, in FIG. 6, the second example of an embodiment of the aortic cannula according to the invention is shown without the hollow-cylindrical part 8 and the fastening section 7. The tetrahedral embodiment of the surface 52a, 52b, 52c, 52d on the side of the fixing rods 5 facing the fluid flow is clearly evident. The outside contour 51 of the fixing rods 5 is also clearly evident.

In both examples of embodiments, the deflecting areas of the four deflecting elements have the same area. This ensures that a similar proportion of the fluid is deflected by each deflecting element and that a uniform distribution of the swirling over the overall length of the cannula tip is achieved.

The hollow-cylindrical part 8 of an aortic cannula according to the invention can also have a curved shape in order to facilitate the introduction and positioning of the cannula head in the vessel, in particular in the aorta.

The invention claimed is:

1. An aortic cannula for delivering fluid into a vessel of the human body, the aortic cannula comprising:
   a. an elongate cannula body that is insertable into the vessel of the human body, into which the fluid is directed, with an orifice, from which the fluid is discharged at the distal end of the basic cannula body in a basic direction of flow defined by the cannula body; and
   b. at least a first deflecting element and a second deflecting element,
      i. which are arranged in front of the orifice within the flow path of the fluid,
      ii. which each have a passage opening aligned relative to the orifice, and
      iii. which each have a deflecting area, which redirects a portion of the fluid which does not flow through the passage opening,
      iv. wherein the area of the passage opening of the first deflecting element is greater than the area of the passage opening of the second deflecting element, and/or wherein the angle of deflection of the deflecting area of the first deflecting element is greater than the angle of deflection of the deflecting area of the second deflecting element, which is arranged behind the first deflecting element in the basic direction of flow.

2. The aortic cannula according to claim 1, wherein the area of the passage opening of the deflecting elements is smaller than or equal to the opening surface of the orifice.

3. The aortic cannula according to claim 1, wherein the overall size of the first deflecting element is greater than the overall size of the second deflecting element, which is arranged behind the first deflecting element in the basic direction of flow.

4. The aortic cannula according to claim 1, wherein each of the first and second deflecting elements has a circular shape.

5. The aortic cannula according to claim 1, wherein the surfaces of the first and the second deflecting elements facing the orifice have a rounded shape.

6. The aortic cannula according to claim 1, wherein four deflecting elements are provided.

7. The aortic cannula according to claim 1, wherein the areas of the deflecting areas of the deflecting elements are substantially equal.

8. The aortic cannula according to claim 1, wherein the deflecting element on the side facing away from the orifice furthest away from the orifice has a rounded surface which is penetrated by the passage opening.

9. The aortic cannula according to claim 1, wherein fixing elements to hold the deflecting elements are provided, which extend from the orifice of the cannula body substantially in the basic direction of flow and on which the deflecting elements are fixed.

10. The aortic cannula according to claim 9, wherein the deflecting elements and the fixing elements have a one-piece design.

11. The aortic cannula according to claim 9, wherein the fixing elements form an outside contour of the cannula tip.

12. The aortic cannula according to claim 9, wherein the deflecting elements and the fixing elements are embodied as a cannula head which has a fastening section for a tube-like cannula body and is connected in a detachable way with the tube-like cannula body.

13. The aortic cannula according to claim 12, wherein the fastening section is embodied as one-piece with a hollow-cylindrical part.

14. The aortic cannula according to claim 9, wherein the fixing elements are formed as oblong rods.

15. The aortic cannula according to claim 9, wherein the fixing elements have a rounded surface towards the interior of the cannula.

16. The aortic cannula according to claim 9, wherein the fixing elements have a tetrahedral surface towards the interior of the cannula.

17. The aortic cannula according to claim 9, wherein individual fixing element sections of the fixing elements are arranged in two successive areas between deflecting elements-offset to each other.

18. A cannula head for an aortic cannula for delivering fluid into a vessel of the human body, the cannula head comprising:
   a. an elongate cannula body that is insertable into the vessel of the human body, into which the fluid is directed, with an orifice from which the fluid is discharged at the distal end of the cannula body in a basic direction of flow defined by the cannula body, the cannula body having a fastening section for a tube-like cannula body and a hollow-cylindrical part; and
   b. at least a first deflecting element and a second deflecting element,
      i. which are arranged in front of the orifice within the flow path of the fluid,
      ii. which each have a passage opening which is aligned relative to the orifice, and
      iii. which each have a deflecting area, which redirects a portion of the fluid which does not flow through the passage opening;
      iv. wherein the area of the passage opening of the first deflecting element is greater than the area of the passage opening of the second deflecting element, and/or wherein the angle of deflection of the deflecting area of the first deflecting element is greater than the angle of deflection of the deflecting area of the second deflecting element, which is arranged behind the first deflecting element in the basic direction of flow.

19. The cannula head according to claim 18, wherein the area of the passage opening of each of the deflecting elements is smaller than or equal to the opening surface of the orifice.

20. The cannula head according to claim 18, wherein the overall size of the first deflecting element is greater than the overall size of the second deflecting element, which is arranged behind the first deflecting element in basic direction of flow.

21. The cannula head according to claim 18, wherein each of the first and the second deflecting elements has a circular shape.

22. The cannula head according to claim 18, wherein the surfaces of the first and second deflecting elements facing the orifice have a rounded shape.

23. The cannula head according to claim 18, wherein four deflecting elements are provided.

24. The cannula head according to claim 18, wherein the areas of the deflecting areas of the deflecting elements are substantially equal.

25. The cannula head according to claim 18, wherein the deflecting element on the side facing away from the orifice furthest away from the orifice has a rounded surface which is penetrated by the passage opening.

26. The cannula head according to claim 18, wherein fixing elements to hold deflecting elements are provided, which extend from the orifice of the hollow-cylindrical part substantially in the basic direction of flow and on which the deflecting elements are fixed.

27. The cannula head according to claim 26, wherein the deflecting elements and the fixing elements have a one-piece design.

28. The cannula head according to claim 26, wherein the fixing elements form an outside contour of the cannula tip.

29. The cannula head according to claim 26, wherein the fixing elements are formed as oblong rods.

30. The cannula head according to claim 26, wherein the fixing elements have a rounded surface towards the interior of the cannula.

31. The cannula head according to claim 26, wherein the fixing elements have a tetrahedral surface towards the interior of the cannula.

32. The cannula head according to claim 26, wherein individual fixing element sections of the fixing elements are arranged in two successive areas between deflecting elements offset to each other.

\* \* \* \* \*